United States Patent [19]
Falk

[11] Patent Number: 4,551,609
[45] Date of Patent: Nov. 5, 1985

[54] SPECTROMETRY PLASMA BURNER

[75] Inventor: Gertrud Falk, Röttenbach, Fed. Rep. of Germany

[73] Assignee: Siemens Aktiengesellschaft, Munich, Fed. Rep. of Germany

[21] Appl. No.: 585,249

[22] Filed: Mar. 1, 1984

[30] Foreign Application Priority Data

Mar. 24, 1983 [AT] Austria .................................. 3310742

[51] Int. Cl.$^4$ ............................. B23K 9/00; H01J 7/24
[52] U.S. Cl. ........................ 219/121 PR; 219/121 PM; 219/121 PP; 315/111.51; 313/231.31; 356/316
[58] Field of Search ...... 219/121 P, 121 PM, 121 PP, 219/121 PN, 121 PQ, 121 PR; 313/231.31, 231.41; 315/111.51, 111.71; 356/315, 316

[56] References Cited

U.S. PATENT DOCUMENTS

| | | | |
|---|---|---|---|
| 3,296,410 | 1/1967 | Hedger | 219/121 PR |
| 3,467,471 | 9/1969 | Greenfield et al. | 219/121 PP |
| 4,147,916 | 4/1979 | Fairbairn | 219/121 PP |
| 4,266,113 | 5/1981 | Denton et al. | 219/121 PQ |
| 4,482,246 | 11/1984 | Meyer et al. | 315/111.51 |

*Primary Examiner*—M. H. Paschall
*Attorney, Agent, or Firm*—Kenyon & Kenyon

[57] ABSTRACT

A plasma burner or torch for emission spectrometry comprises an induction coil for generating a plasma, an outer jacket, an inner jacket coaxial therewith, a sleeve inside the inner jacket and coaxial therewith, a capillary tube inside the sleeve and oriented along the axis of symmetry, a cooling gas feed line, a plasma gas feed line, and an aerosol gas feed line. The distance of the sleeve from the inner jacket of the plasma burner is advantageously smaller than the distance between the sleeve and the capillary tube. The sleeve preferably consists essentially of quartz. In such a plasma torch, the rate of consumption of the plasma gas as well as of the cooling gas is reduced, while the detection power of the device for elements such as boron, iron, magnesium, phosphorous and zinc is comparable to conventional standard burners.

7 Claims, 1 Drawing Figure

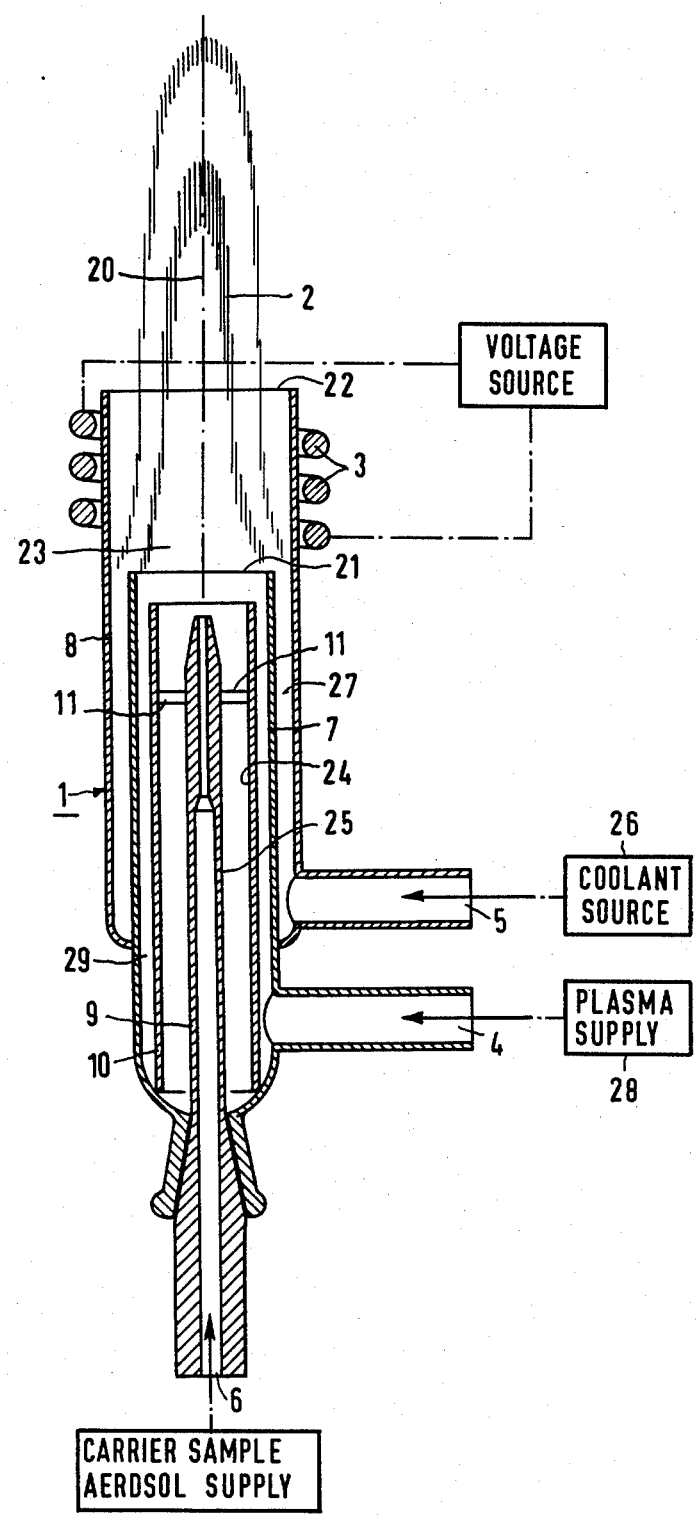

SPECTROMETRY PLASMA BURNER

BACKGROUND OF THE INVENTION

This invention relates to a device used in spectrometry for exciting a chemical element to emit electromagnetic radiation.

Such a device, commonly known as a plasma burner or torch, is employed in ICP emission spectrometry for detecting elements such as boron, iron, magnesium, phosphorous and zinc. A plasma burner or torch generally comprises an elongate capillary tube, an inner jacket surrounding the capillary tube coaxially therewith, an outer jacket surrounding the inner jacket and coaxial therewith and an induction coil for generating a plasma. A cooling gas is fed to a space between the inner jacket and the outer jacket, while a plasma gas is conveyed to a space between the inner jacket and the capillary tube, the capillary tube serving to guide into the plasma burner an aerosol consisting of a carrier gas and particles of a chemical element to be analysed. A standard plasma burner, as described by S. Greenfield et al., *Analyst*, Vol. 89, pages 716 to 720 (1964) operates with nitrogen as a cooling gas and argon as the plasma gas. The plasma is generated in the interior of the burner by an induction coil having two or three turns closely surrounding the outer jacket of the burner. A high voltage alternating current applied to the coil generates in the burner a changing magnetic field in turn bringing about an electric ring voltage perpendicular to the axis of the burner. This ring voltage is on the order of 20 to 30 volts and maintains the plasma after ignition has occurred, the plasma taking the form of an elipsoid.

The plasma gas and the cooling gas cause in the flow direction an elongation of the plasma ellipsoid and a considerable flattening thereof in the counterflow direction. The resulting geometry of the plasma ellipsoid enables the aerosol gas stream emanating from the mouth of the capillary tube to pierce the ellipsoid in the center thereof so that it assumes an annular shape. Only in this case is the aerosol gas sufficiently heated to excite the subject chemical element contained in the aerosol sample to emit electromagnetic radiation. The light emission due to the excitation can then be analyzed qualitatively as well as quantitatively by means of a spectrophotometer.

In the event the plasma ellipsoid is not pierced by the aerosol gas, the ellipoid acts like a solid body on the flow of the aerosol, thereby causing a major portion thereof to flow past the plasma unheated.

The pressure distribution in the plasma and the magnetically induced backflow thereof are determined in part by the flow of the plasma gas and of the cooling gas. For example, if the flow of the plasma gas and the cooling gas has a tangential component, the backflow velocity is reduced, which reduction facilitates the introduction of the aerosol gas. It is to be noted that the primary purpose of the cooling gas is to cool the quartz wall which is in contact with the plasma gas.

Argon/nitrogen burners require an argon flow of approximately 5 to 10 liters per minute and a nitrogen gas flow of approximately 15 to 20 liters per minute. The total consumption of gas is considerable. It is 2 to 5 times as large as the plasma gas flow. One method of reducing the gas consumption, particularly the consumption of expensive argon gas, has involved reducing the dimensions of the burner. However, this solution has a negative affect on the stability of the plasma. To control the plasma stability the amount of aerosol gas introduced into the plasma must be decreased, which decrease has the effect of lowering the detection sensitivity or power. In general, the performance of a small plasma burner is not as high as the performance of a standard burner. See A. D. Weiss et al., *Analytica Chimica Acta*, Vol. 124, pages 245 to 258 (1981). Some prior art plasma burners are provided with water cooling, as described by Guy R. Kornbulm in the article "Reduction of Argon Consumption by a Water-Cooled Torch in Inductively Coupled Plasma Emission Spectrometry, "*Analytical Chemistry*, Vol. 51, No. 14, December 1979, pages 2378 to 2381, and by H. Kawaguichi in the article "Water-Cooled Torch for Inductively Coupled Plasma Emission Spectrometry," *Analytical Chemistry*, Vol 52, 1980, pages 2440 to 2442.

In such plasma burners or torches, the water implemented cooling of the outer wall can reduce gas consumption substantially. However, the flow of cooling gas cannot be eliminated altogether because otherwise the flow and pressure conditions of the plasma are detrimentally altered.

An object of the present invention is to provide an improved plasma burner or torch of the above described type in which gas consumption is markedly reduced, thereby lowering the high operating costs of ICP emission spectrometry.

An additional object of the present invention is to provide such a plasma burner which retains a high level of performance and analytical capability.

SUMMARY OF THE INVENTION

In accordance with the present invention, a device used in spectrometry for exciting a chemical element to emit electromagnetic radiation includes a sleeve disposed between a capillary tube and an inner jacket, the sleeve being coaxial with an outer jacket, the inner jacket and the capillary tube. More particularly, the spectrometry device comprises a preferably cylindrical outer jacket having a longitudinal axis of symmetry and an opening at one end. A preferably cylindrical inner jacket is at least partially disposed inside the outer jacket coaxially therewith, the inner jacket being longitudinally staggered with respect to the outer jacket to form a cylindrical burner space defined in part by the end of the outer jacket provided with an opening and by an end of the inner jacket disposed inside the outer jacket. The inner jacket is also formed with an opening at its end inside the outer jacket. The inner jacket is radially spaced from the outer jacket to form a first annular space communicating with the cylindrical burner space. An elongate capillary tube is at least partially disposed in the inner jacket and aligned along the axis of symmetry of the outer jacket. The capillary tube has a mouth at one end juxtaposed to the cylindrical burner space. The sleeve is substantially cylindrical and is disposed in the inner jacket coaxially therewith. The sleeve is radially spaced from the inner jacket to form therewith a second annular space communicating with the cylindrical burner space. an induction coil surrounds the outer jacket in the region of the cylindrical burner space, an electrical power supply being operatively connected to the coil for energizing the coil with a high voltage alternating current. A first gas supply is connected to the outer jacket for feeding a coolant to the first annular space, while a second gas supply is connected to the inner jacket for feeding a plasma gas to the second annular space. A third gas supply feeds to the capillary tube an aerosol containing the chemical element to be excited.

In accordance with another feature of the present invention, the distance between the sleeve and the inner jacket is smaller than the distance between the sleeve and the capillary tube.

Pursuant to another feature of the present invention, a mounting ring is provided for centering the sleeve with respect to the capillary tube, the inner jacket and the outer jacket. The ring preferably consists essentially of aluminum oxide. The ring engages the sleeve at an inner surface thereof and the capillary tube at an outer surface thereof.

In a plasma burner or torch according to the present invention, gas consumption is considerably reduced, while performance is not detrimentally affected to any significant extent.

BRIEF DESCRIPTION OF THE DRAWING

The sole FIGURE of the drawing is a schematic longitudinal cross section view of a plasma burner or torch according to the present invention.

DETAILED DESCRIPTION OF THE INVENTION

A plasma burner or torch 1 comprises a substantially cylindrical outer jacket 8 having a longitudinal axis of symmetry 20, a substantially cylindrical inner jacket 7 coaxial with outer jacket 8, an elongate capillary tube 9 located on axis 20 and an induction coil 3 having two to three turns wrapped around outer jacket 8. Inner jacket 7 and outer jacket 8 each have an opening 21 and 22 at one end. Inner jacket 7 is staggered with respect to outer jacket 8, thereby forming or defining a cylindrical burner chamber 23 in the region of induction coils 3.

In accordance with the present invention the plasma burner 1 is provided with a cylindrical sleeve 10 surrounding capillary tube 9 and disposed in inner jacket 7 coaxially therewith. A mounting ring 11 preferably consisting essentially of aluminum oxide is provided for centering sleeve 10 with respect to capillary tube 9 as well as with respect to inner jacket 7 and outer jacket 8. Ring 11 engages an inner surface 24 of sleeve 10 and an outer surface 25 of capillary tube 9.

A coolant source 26 is connected to outer jacket 8 by means of a feed line or conduit 5 for supplying a cooling gas such as nitrogen to an annular space 27 defined by inner jacket 7 and outer jacket 8. Similarly a plasma supply 28 is connected to inner sleeve 7 via a feed line or conduit 4 for feeding a plasma gas such as argon to an annular space 29 formed between inner jacket 7 and sleeve 10. An aerosol supply 30 is connected to an outer end of capillary tube 9 via a conduit 6 for feeding to the capillary tube an aerosol consisting of a carrier gas such as argon and particles of a chemical element such as boron, iron, magnesium, phosphorous or zinc to be spectrometrically analyzed.

The plasma gas stored in supply 28 and the carrier gas for transporting the chemical sample can generally be any rare gas.

Sleeve 10 preferably consists essentially of quartz and is disposed at a distance from inner jacket 7 less than the distance of the sleeve from capillary tube 9.

Feed lines 4 and 5 are preferably connected to inner jacket 7 and outer jacket 8, respectively, at the ends thereof opposite openings or mouths 21 and 22. Feed lines 4 and 5 are connected to jackets 7 and 8 at an angle to produce a tangential component of plasma and cooling gas flow, as well as a longitudinal component in the direction towards cylindrical burner chamber 23. The production of a tangential component of plasma gas flow is enabled and facilitated by the formation of a relatively thin annular space 29, due to the disposition of sleeve 10 between inner jacket 7 and capillary tube 9. In conventional plasma gas burners or torches, the tangential component of plasma gas flow is small, if not entirely nonexistent, and the plasma gas flows substantially only longitudinally over the entire cross-sectional area between the capillary tube and the inner jacket.

In a plasma burner in accordance with the present invention, the changed flow conditions result in a reduced resistance to the flow of aerosol gas through the center of a plasma ellipsoid 2 located partially in cylindrical burner space 23 and extending in part from the mouth 22 of outer jacket 8. Because of the reduced resistance to aerosol gas flow, 0.6 to 0.7 liters of aerosol per minute can still be introduced into the plasma burner with a plasma gas flow 2 to 3 liters per minute of argon. The plasma in a plasma torch according to the present invention burns precisely as quitely as in a conventional burner, while a conventional burner requires 7 to 8 liters of argon per minute. Argon consumption is therefore reduced on the order of 60 to 70%.

A plasma burner or torch according to the present invention also enables a reduction in the amount of nitrogen used for cooling purposes. Nitrogen consumption in a conventional burner is 20 liters per minute, while the nitrogen consumption in a burner according to the present invention is about 11 liters per minute. This translates to a 50% saving in the amount of nitrogen used.

Because the analytical power or sensitivity of a plasma burner or torch pursuant to the present invention remains high while the gas consumption is decreased, and because the spectrum of applications with respect to the chemical elements to be analyzed is wide, the device is particularly well-suited for routine analyses.

What is claimed is:

1. In a device used in spectrometry for exciting a chemical element to emit electromagnetic radiation, said device having an outer jacket, an inner jacket coaxial therewith, an axially disposed capillary tube, a first feed line for conveying plasma gas, a second feed line for conveying cooling gas, a third feed line for conveying aerosol including the chemical element to be excited, and an induction coil wound around the outer jacket at one end thereof for generating the plasma, the improvement comprising insulating means for forming a dead space surrounding said capillary tube, said insulating means including a sleeve disposed between the capillary tube and the inner jacket, said sleeve being coaxial with the outer jacket, said inner jacket and said capillary tube, said sleeve being radially spaced from said capillary tube to form said dead space therewith, said insulating means further including a solid ring for centering said sleeve with respect to said capillary tube and for closing off said dead space at an end thereof proximate to the induction coil, said ring engaging said sleeve at an inner surface thereof and said capillary tube at an outer surface thereof.

2. The improvement defined in claim 1 wherein the distance between said sleeve and said inner jacket is smaller than the distance between said sleeve and said capillary tube.

3. The improvement defined in claim 2 wherein said ring consists essentially of aluminum oxide.

4. The improvement defined in claim 1 wherein said ring is made of aluminum oxide.

5. A device used in spectrometry for exciting a chemical element to emit electromagnetic radiation, comprising:
- a substantially cylindrical outer jacket having a longitudinal axis of symmetry and a first opening at one end;
- a substantially cylindrical inner jacket at least partially disposed inside said outer jacket coaxially therewith, said inner jacket being longitudinally staggered with respect to said outer jacket to form a cylindrical space defined in part by said one end of said outer jacket and by an end of said inner jacket, said end of said inner jacket being provided with an opening, said inner jacket being radially spaced from said outer jacket to form a first annular space communicating with said cylindrical space;
- an elongate capillary tube at least partially disposed in said inner jacket and aligned along said axis, said capillary tube having a mouth at an end juxtaposed to said cylindrical space;
- insulating means for forming an annular dead space surrounding said capillary tube, said insulating means including a substantially cylindrical sleeve disposed in said inner jacket coaxially therewith, said sleeve being radially spaced from said inner jacket to form therewith a second annular space communicating with said cylindrical space, said sleeve being radially spaced from said capillary tube to form said dead space therewith, said insulating means further including a solid ring for centering said sleeve with respect to said capillary tube and for closing off said dead space at an end thereof proximate to said cylindrical space, said ring engaging said sleeve at an inner surface thereof and said capillary tube at an outer surface thereof, said sleeve having an end engaging said inner jacket at an end thereof opposite said second opening to close said dead space at an end thereof opposite said ring;
- an induction coil surrounding said outer jacket in the region of said cylindrical space;
- electrical power means operatively connected to said coil for energizing said coil with a high voltage alternating current;
- first gas supply means connected to said outer jacket for feeding a coolant to said first annular space;
- second gas supply means for feeding a plasma gas to said second annular space; and
- third gas supply means for feeding to said capillary tube an aerosol containing the chemical element to be excited.

6. The device defined in claim 5 wherein the distance between said sleeve and said inner jacket is smaller than the distance between said sleeve and said capillary tube.

7. The device defined in claim 5 wherein said ring consists essentially of aluminum oxide.

* * * * *